United States Patent [19]
Dumoulin et al.

[11] Patent Number: 5,526,812
[45] Date of Patent: Jun. 18, 1996

[54] DISPLAY SYSTEM FOR ENHANCING VISUALIZATION OF BODY STRUCTURES DURING MEDICAL PROCEDURES

[75] Inventors: Charles L. Dumoulin, Ballston Lake; Robert D. Darrow, Scotia; William J. Adams, Clifton Park, all of N.Y.

[73] Assignee: General Electric Company, Schenectady, N.Y.

[21] Appl. No.: 549,320

[22] Filed: Oct. 27, 1995

Related U.S. Application Data

[63] Continuation of Ser. No. 340,784, Nov. 17, 1994, abandoned, which is a continuation-in-part of Ser. No. 78,335, Jun. 21, 1993, abandoned.

[51] Int. Cl.$^6$ .................................................. A61B 6/00
[52] U.S. Cl. .............................. 128/653.100; 606/130; 345/7; 345/9; 348/77
[58] Field of Search ........................... 128/653.1, 653.2; 606/130; 348/77; 345/1, 7–9, 113, 114; 364/413.13, 413.22

[56] References Cited

U.S. PATENT DOCUMENTS

| | | | |
|---|---|---|---|
| 4,340,878 | 7/1982 | Spooner et al. | 345/7 |
| 4,398,799 | 8/1983 | Swift | 345/9 |
| 4,544,243 | 10/1985 | Munnerlyn | 345/7 |
| 4,722,056 | 1/1988 | Roberts et al. | 606/130 |
| 5,153,569 | 10/1992 | Kawamura et al. | 345/8 |
| 5,230,338 | 7/1993 | Allen et al. | 606/130 |
| 5,233,299 | 8/1993 | Souza et al. | |
| 5,245,319 | 9/1993 | Kilian | 345/9 |

OTHER PUBLICATIONS

IBM Technical Disclosure Bulletin, "Three–Dimensional Graphic Display", vol. 31, No. 6 Nov. 1988, pp. 318–319.

"Interactive Stereotactic Surgical system for the Removal of Intracranial Tumors Utilizing the CO2 Laser and CT–Derived Database" by B. A. Kall, P. J. Kelly, and S. J. Goerss, IEEE Transactions on Biomedical Engineering, vol. BME–32, No. 2, pp. 112–116, 1985.

"Comprehensive Computer–Assisted Data Collection Treatment Planning and Interactive Surgery" by B. A. Kall, P. J. Kelly, and S. J. Goerss, Medical Imaging, vol. 767, pp. 509–514, 1987.

"A Frameless Stereotaxic Operating Microscope for Neurosurgery" by E. M. Friets, J. W. Strohbehn, J. F. Hatch, and D. W. Roberts, IEEE Transactions of Biomedical Engineering, vol. 36, No. 6, pp. 608–617, Jun. 1989.

"The Flock of Birds" Installation and Operation Guide, Ascension Technology Corporation, Jul. 5, 1992, in the Introduction pp. 1–3, Appendix 1, p. 89 and Appendix 3, p. 93.

"Portable, Low Cost Devices for Videotaping, Editing and Displaying Field Sequential Stereoscopic Motion Pictures and Video" by M. Starks, Stereoscopic Displays and Applications Proc., SPIE vol. 1256, pp. 266–271, 1990.

*Primary Examiner*—Ruth S. Smith
*Attorney, Agent, or Firm*—Lawrence P. Zale; Marvin Snyder

[57] ABSTRACT

An interactive display system superimposes images of internal structures on a semi-transparent screen through which a surgeon views a patient during a medical procedure. The superimposed image is derived from image data obtained with an imaging system. An invasive device is also tracked and displayed on the semi-transparent screen. A ray extending through the invasive device can also be displayed which shows the intended path of the invasive device. The image is registered with the surgeon's view of the patient and displayed in real-time during a medical procedure. This allows the surgeon to view internal and external structures, the relation between them, the proposed path of the invasive device, and adjust the procedure accordingly. A second embodiment employs stereoscopic viewing methods to provide three-dimensional representations of the radiological images superimposed on the semi-transparent screen through which the surgeon views the patient.

9 Claims, 2 Drawing Sheets

DISPLAY SYSTEM FOR ENHANCING VISUALIZATION OF BODY STRUCTURES DURING MEDICAL PROCEDURES

CROSS REFERENCE TO RELATED APPLICATIONS

This application is a continuation of application Ser. No. 08/340,784 filed Nov. 17, 1994 now abandoned, which is a continuation-in-part (CIP) of "A Display System For Enhancing Visualization of Body Structures During Medical Procedures" by C. L. Dumoulin, R. D. Darrow, W. J. Adams, Ser. No. 08/078,335, filed Jun. 21, 1993 now abandoned. This application is related to U.S. patent applications "An Interactive Digital Arrow (D'Arrow) Three-dimensional (3D) Pointing Device" by C. Dumoulin, R. Darrow, W. Adams Ser. No. 08/240,783 filed Nov. 17, 1994 filed along with this application; and "Computer Graphic and Live Video System for Enhancing Visualization of Body Structures During Surgery" by Chris Nafis, Tim Kelliher, Harvey Cline, Bill Lorensen, David Altobelli, Ron Kikinis, Robert Darrow and Charles Dumoulin, Ser. No. 08/342,690, filed Nov. 24, 1994, both hereby incorporated by reference and assigned to the present assignee.

This application is also related to "System For Displaying Solid Cuts For Surfaces of Solid Models" by William E. Lorensen, Harvey E. Cline, Bruce Teeter, and Siegwalt Ludke, Ser. No. 07/812,394 filed Dec. 23, 1991, hereby incorporated by reference and assigned to the present assignee.

BACKGROUND OF THE INVENTION

1. Field of the Invention

The present invention relates to a system for aiding a medical practitioner, such as a surgeon, in visualizing anatomical structures during medical procedures and more specifically to a system which allows the practitioner to view, in real time, both internal and external anatomical structures.

2. Discussion of Prior Art

Presently, during surgery and other medical procedures such as endoscopy, biopsy and implantation, physicians view several static radiographic views of the patient in the operating room. Typically these are transparent film renderings of magnetic resonance (MR), computed tomography (CT), conventional X-ray images or ultrasound images. Since these images are two dimensional static images, the physicians must determine the actual three-dimensional (3D) location and shape of desired internal structures within the patient from the 2D images which they are viewing. The surgeon conceptually constructs a 3D model of the internal structures and correlates these internal structures with visible external structures of the patient where they must cut. This is often difficult because the scale and the orientation of the 2D image may differ from what the surgeon is seeing, and the surgeon may not be able to view both the patient and the medical diagnostic images simultaneously.

Another technique employed in localization of internal structures during surgery is known as stereotactic surgery as described in "Interactive Stereotactic Surgical System for the Removal of Intracranial Tumors Utilizing the $CO_2$ Laser and CT-Derived Database" by B. A. Kall, P. J. Kelly, and S. J. Goerss, IEEE Transactions on Biomedical Engineering, vol. BME-32, no. 2, pp 112–116, 1985; and "Comprehensive Computer-Assisted Data Collection Treatment Planning and Interactive Surgery" by B. A. Kall, P. J Kelly, and S. J. Goerss, Medical Imaging, vol. 767 pp. 509–514, 1987. With this approach, a rigid mechanical frame is attached to the patient before a CT or MR procedure. The frame and its landmarks can be seen in the resulting images. Mechanisms on the frame position a probe at specific location within the image. The disadvantages of this approach are that the frame limits access to the patient, and the images are static images which do not follow the patient if he moves during surgery.

A third technique used for localization of internal structures is described in "A Frameless Stereotaxic Operating Microscope for Neurosurgery" by E. M. Friets, J. W. Strohbehn, J. F. Hatch, and D. W. Roberts, IEEE Transactions on Biomedical Engineering, vol. 36., no. 6, pp 608–617, June 1989.

Three dimensional models of anatomical structures can be created from data of different medical imaging modalities as described in the application Ser. No. 07/812,384 listed above in the "CROSS REFERENCE TO RELATED APPLICATIONS". These applications describe creating and manipulating models of internal structures of patients and providing images of selected structures at desired orientations to an operator. These allow visualization of internal structures as solid models.

Currently there is a need for a system to aid physicians in surgery and other medical procedures which interactively displays computer generated representations of internal structures in correct relation with external structures of the patient, and permits visualization of actual and hypothetical paths of invasive devices.

OBJECTS OF THE INVENTION

An object of the present invention is to provide a system which aides in surgery by simultaneously superimposing an image of internal structures upon external structures even if the patient changes their position or if the operators change their viewing angles.

Another object of the present invention is to provide an interactive system which displays desired internal structures upon external structures, having the same scale and viewed from the same orientation angles.

Another object of the present invention is to provide a surgeon a "heads up" display of radiological images superimposed upon external structures of a patient within his field of view without the use of cumbersome headgear.

Another object of the present invention is to provide a display system which is integrated with an invasive device for providing visualization of the invasive device relative to internal structures of the subject.

SUMMARY OF THE INVENTION

A real-time surgery apparatus for displaying interactive internal and external images of a patient employs a semi-transparent display screen allowing an operator to simultaneously view exposed surfaces and computer generated images of internal structures of a patient. A symbol representing an invasive device is superimposed upon the computer generated image at a location properly displayed with respect to both the internal and external structures.

A medical imaging device or computer assisted design (CAD) system provides three-dimensional (3D) imaging data of internal structures of the patient to a workstation. The three-dimensional position and orientation of the patient, semi-transparent screen, operator's eyes and an invasive device intended to be inserted into the patient, are monitored in real-time. The workstation creates three-dimensional (3D) computer generated models of the patients internal structures which may be manipulated without further need for the medical imaging device. Two-dimensional computer generated images of the models are interactively oriented and scaled so that their display on a semi-transparent display device coincides with the operator's visual image of the patient through the semi-transparent screen.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawing in which:

DETAILED DESCRIPTION OF THE INVENTION

Figure 1:
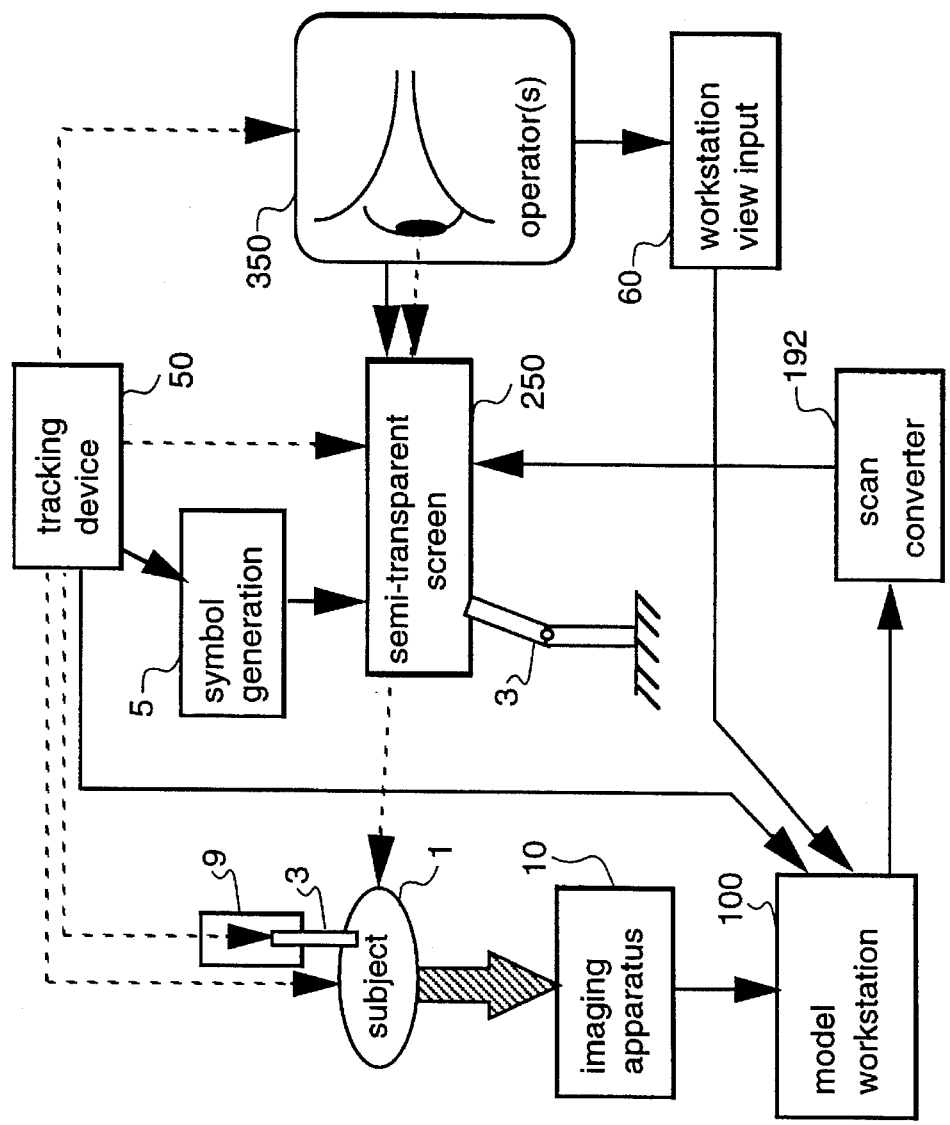
FIG. 1 is a simplified block diagram of a first embodiment of a medical display apparatus according to the present invention.

In FIG. 1, a subject, or patient 1 on which a medical procedure such as surgery is to be performed, is scanned by a medical imaging apparatus 10 which may be a magnetic resonance (MR) imaging apparatus, a computed axial tomography (CAT) apparatus, a positron emission tomography (PET) or similar imaging device capable of creating multi-dimensional volumetric data such as 3-dimensional (3-D) data, from internal structures of the patient. After imaging, apparatus 10 provides the volumetric data to a model workstation 100. Once the volumetric data has been provided to model workstation 100, further need for imaging apparatus 10 imaging apparatus is no longer required. This is important since some medical procedures need not be performed with the patient situated within the confines of an imaging apparatus, which can be constricting as in the case of MR imaging. In alternative embodiments, imaging apparatus 10 may be interactively employed during the medical procedure. Model workstation 100 stores the volumetric data and creates computer generated models from the data capable of being scaled, rotated and otherwise manipulated, without the further need for imaging apparatus 10.

An operator 350, such as a physician or medical assistant, monitors patient 1. A semi-transparent screen 250 is interposed between patient 1 and operator 350. A tracking device 50 which monitors and tracks operator 350, semi-transparent screen 250 and patient 1 determines a location and orientation, being roll α, pitch θ, and yaw φ of operator 350, subject 1, semi-transparent screen 250 and invasive device 3. Tracking device 50 may be a 6-degrees of freedom tracking device as described "The Flock of Birds" Installation and Operation Guide, Ascension Technology Corporation, Jul. 5, 1992, in the Introduction pp. 1–3, Appendix 1, p. 89 and Appendix 3, p. 93.

Patient 1 is assumed to be at the origin of the Cartesian coordinate system (x,y,z)=(0,0,0), therefore all locations relative to the patient 1 are simply the (x,y,z) location. The location and orientation of patient 1, semi-transparent screen 250, and operator 350 are interactively provided to model workstation 100 by tracking device 50. The location and orientation may also be provided manually to model workstation(s) in different embodiments.

Model workstation 100 processes the 3D volumetric data it receives and creates selected renderings of the data. One rendering method determines surfaces between differing types of tissue. Connectivity of similar types of tissue adjacent to one another is then determined. Differentiation of tissue types based on the nature of the signal in the three-dimensional image data is known as segmentation. When the 3-D volumetric data has been segmented into internal structures, each internal structure may be treated as a separate solid object by model workstation 100. The model workstation has the capability of selectively displaying desired internal structures, color coding structures and severing, rotating and translating internal structures in order to manipulate these images in a desired manner to provide visualization to an operator working model workstation 100.

An alternative rendering method generates two-dimensional projections of selected features within the three-dimensional data set as described in U.S. Pat. No. 5,233,299 Aug. 3, 1993 "Projection Methods for Producing Two-Dimensional Images from Three-Dimensional Data" by S. P. Souza, W. J. Adams and C. L. Dumoulin. For example, two-dimensional projection angiograms can be extracted from a three-dimensional phase contrast or time-of-flight magnetic resonance angiogram. Several projection algorithms are possible. These include the detection of the maximum pixel intensity along a selected projection ray through the three-dimensional data, determination of the average pixel intensity of a selected projection ray and the determination of the standard deviation of all pixels along a selected projection ray.

Model workstation 100 receives input data from a workstation view input device 60, and from tracking device 50 following the position and orientation to select the orientation for displaying internal structures of patient 1. Workstation view input device 60 may be a computer pointing device such as a mouse or trackball, or any input device which indicates planes in which to cut the images and a viewing angle and scale. Model workstation 100 synthesizes an interactive computer generated image of internal structures of patient 1 which coincide with the real-time scene viewed by operator 350. A symbol generation device 5 generates a symbol showing the position, and orientation of invasive device 3. Optionally, a ray extending from the invasive device 3 may be drawn indicating the current intended path of invasive device 3.

The interactive computer generated image may be converted from a computer monitor signal, such as an RGB computer monitor signal, to a video format by passing it through a scan converter 192 (shown in phantom), depending on the required display format of semi-transparent screen 250. The computer generated image is provided to semi-transparent screen 250 which is interposed between patient 1 and operator 350. Semi-transparent screen 250 provides a desired mixture of external structures of patient 1 seen by operator 350 and the computer generated image from model workstation 100. Semi-transparent screen 250 may receive input signals from the operator, for example, through workstation view input 60. This may involve the degree of transparency of each image, or any of various other special effects. One very useful special effect is a movable window which has 0% transparency (100% opaqueness) superimposed upon another image. When the window image is of internal structures superimposed upon external structures, it creates the illusion of external structures cut away within the window, exposing underlying internal structures. Other conventional video special effects may also be employed. Semi-transparent screen 250 allows operator 350 to visualize both internal and external structures simultaneously. The resulting scene witnessed by operator 350 is an interactive real-time image of patient 1, even if the patient moves during the medical procedure. Since internal structures and their relation to exposed external structures are simultaneously displayed, a surgeon using the present invention will perceive a very accurate indication of where he should cut through external structures to arrive at a desired internal structure while avoiding vital internal structures.

Figure 2:
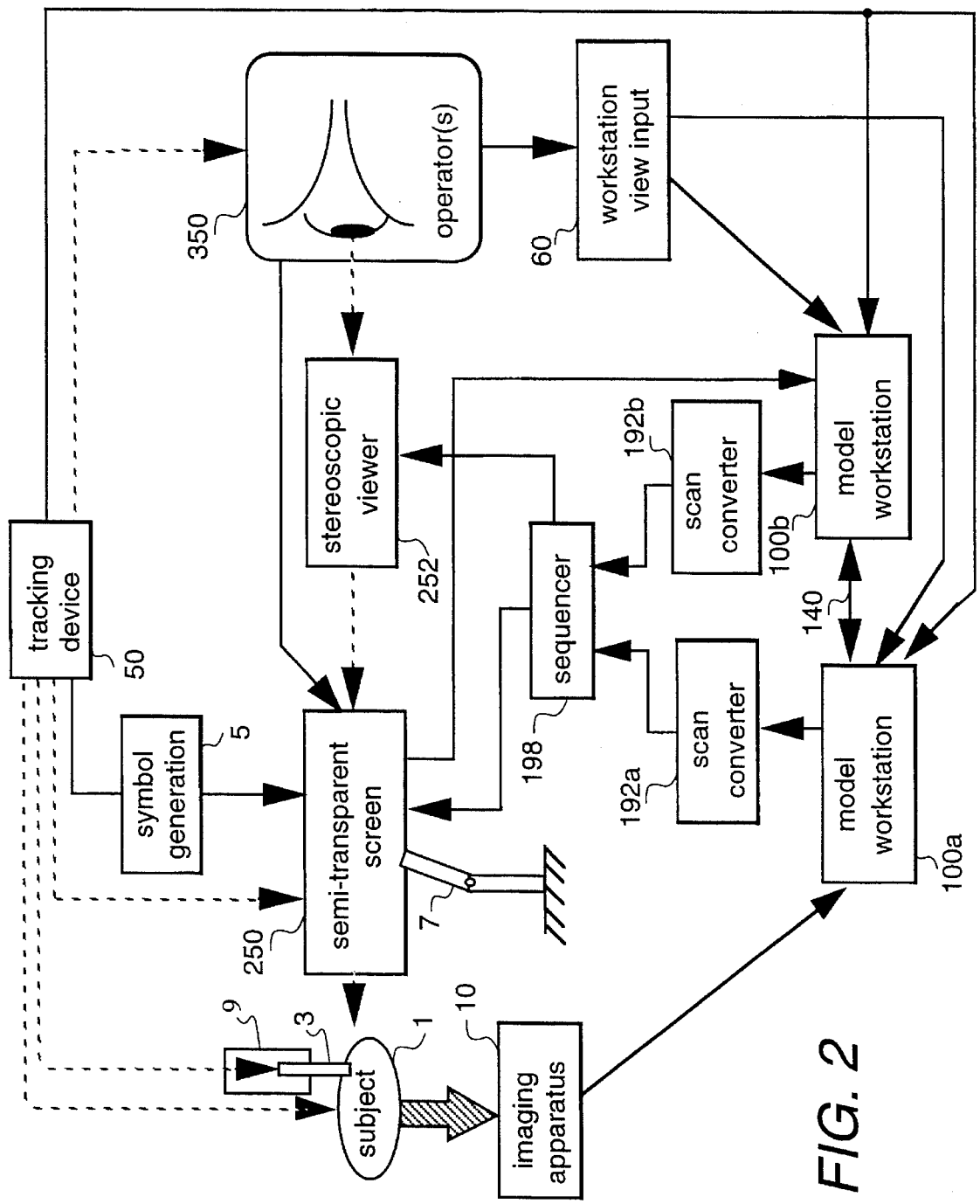
FIG. 2 is a simplified block diagram of a second embodiment of a medical display apparatus according to the present invention.

FIG. 2 illustrates an alternative embodiment of the present invention in which operator 350 receives a stereoscopic view of internal and external structures of patient 1. Each of the eyes of operator 350 differs in its orientation with relation to the patient therefore a different view is provided to each eye. Tracking device 50 tracks the location $(x_1,y_1,z_1)$ and orientation angles $(\alpha_1, \phi_1, \theta_1)$ of a first and second eye of operator 350, patient 1, semi-transparent screen 250 and invasive device 3. The location and orientation of the operator's second eye can be measured independently by tracking device 50; or the location and orientation of the first eye can be used to compute the location and orientation of the second eye. The locations and orientations are fed to a first model workstation 100a, and a second model workstation 100b which create a right and left computer graphic image at locations $(x_1,y_1,z_1)$, $(x_2,y_2,z_2)$, respectively, and orientations $(\alpha_1, \phi_1, \theta_1)$ $(\alpha_2,\phi_2,\theta_2)$, respectively, corresponding to the views of each eye of operator 350, respectively.

A symbol generation device 5 receives the position and orientation of invasive device 3 and displays a symbol in the proper position and orientation on semi-transparent screen 250. The symbol may be extended by a ray which indicates the proposed path of invasive device 3. Control signals from workstation view input 60 and imaging apparatus 10 can be sent to both first model workstation 100a, which in turn propagates the control signals to second model workstation 100b via communications path 140, or alternatively, the control signals can be sent directly to both model workstations directly.

The left and right computer generated image, pertaining to a left and right view, respectively, are converted to video format if required by semi-transparent screen 250. This is accomplished by scan converters 192a, 192b (shown in phantom) which pass the converted computer generated signals to a sequencer 198. Sequencer 198 may be a conventional video sequencer as described in "Portable, Low Cost Devices for Videotaping, Editing and Displaying Field Sequential Stereoscopic Motion Pictures and Video" by M. Starks, Stereoscopic Displays and Applications Proc. SPIE Vol. 1256, pp. 266–271, 1990.

Sequencer 198 passes the left computer generated image to semi-transparent screen 250. Sequencer 198 then passes the right computer generated image to semi-transparent screen 250. Sequencer 198 alternates many times per second, in synchronization, between right and left views.

The image displayed on semi-transparent screen 250 is time multiplexed to produce an image to the left eye and right eye of the operator in an alternating fashion. A stereoscopic viewer 252 is synchronized to the sequencer 198 and operates to block the vision of the operator's left or right eye allowing the opposite eye to view the image on semi-transparent screen 250 for an instant and vice-versa. This allows operator 350 to see the left image with the left eye while the right eye sees nothing and the right image with the right eye while the left eye sees nothing in rapid succession. This creates a stereoscopic illusion, adding the dimension of depth perception in viewing the image displayed on semi-transparent screen 250. Depth perception is very valuable in surgery since it adds a dimension that assists in visually localizing structures, which is especially important in complex, delicate surgery.

For both embodiments of the invention the computer image must be registered (coincide) with the external structures as viewed by operator 350. Initialization may be accomplished by manual input from the operator to rotate, translate and scale the computer generated image(s) until they coincide with the scene observed through the semi-transparent screen, or by employing tracking device 50 to set initial parameters.

Once the 3D model and the visual image of patient 1 are aligned, tracking device 50 keeps the view angles and field of view consistent. This allows real-time interactive synchronization between the operator's view of patient 1 and the computer generated image(s).

Since the image of each internal structure can be segmented into what resembles a solid object, it may be manipulated as a solid object. In the case of structures of a patient, a surgeon may acquire data from the patient by medical imaging, then plan surgery by manipulating the models to plan a desired result before surgery. This is common in complex reconstructive surgery. Once the plan is determined, it may be stored and played back during surgery. The images of internal structures are interactively oriented and scaled to coincide with the actual patient.

A user employs a workstation view input device 60 of FIGS. 1 and 2, respectively to select planes in which to cut the structures in the model, to select a three-dimensional orientation of the model, and to select screen cut planes which define a workstation viewing region. The model workstation can incorporate a clipping circuit to determine points within the model cut planes, a rotation circuit to rotate points and normal vectors, a segmentation processor, and a shading circuit which determines shading based upon the orientation of the normal vector at each point. In addition a screen clipping circuit can be used to determine points within a region defined by the screen cut planes. The model workstation also can include a display circuit to create video signals which, when propagated to a suitable display device, generate images of multiple surfaces that are within the desired display region and the screen cut planes.

In radical surgery such as ablative surgery, or massive trauma cases, there is little structure which remains to correctly determine what a normal anatomy should be. In these cases, an additional model workstation may have a model of normal structures stored which may be mixed with the other images being displayed to act as a guide in reconstructive surgery. This may be implemented by additional workstations or model manipulation boards.

In the present embodiments of the invention, semi-transparent screen 250 is interposed between operator 350 and patient 1. Screen 250 can be constructed with a liquid crystal display or it can be comprised of a partially silvered mirror reflecting an image from a video monitor. Semi-transparent display 250 can be constructed as a relatively large device having dimensions approximately equal to that of the region of interest of patient 1, or alternatively it can be of small dimension and placed relatively close to the operator's eyes, perhaps incorporated into headgear or eyewear.

In one embodiment of the present invention, the semi-transparent screen is attached to a moveable arm 7 which allows the screen to be placed in any location between patient 1 and operator 350. This permits usage of the invention which would be impossible with head-mounted displays. For example, if semi-transparent screen 250 was constructed of a material which was a writeable surface, operator 350 could use an ink marker to trace or annotate regions of interest (e.g. location of an incision) which are visible to others nearby.

Another use of the present invention which would not be possible with a head-mounted display is to use the position and orientation of the display screen to determine the image displayed on the screen. Input device 60 then may be used to adjust the depth of the image plane within the patient. This can therefore be used to scan through the patient looking for internal structures and determining if the proposed path of the invasive device is correct.

Optionally, an invasive positioner 9 is added to the system which holds the invasive device. This also is tracked by tracking means 50 such that the position and orientation of the invasive device is monitored and provided to the model workstation(s). Preferable points to track are the endpoint and at least one other point of the invasive positioner 9 to determine the orientation along with the position of the invasive device.

While several presently preferred embodiments of the novel visualization system have been described in detail herein, many modifications and variations will now become apparent to those skilled in the art. It is, therefore, to be understood that the appended claims are intended to cover all such modifications and variations as fall within the true spirit of the invention.

What is claimed is:

1. A interactive medical apparatus for displaying interactive images of image data of internal structures of a patient at a dynamically changing subject position, to be viewed at an dynamically changing observer viewpoint coinciding with an external view of said patient comprising:
   a) imaging means for acquiring image data of the internal structures of the patient
   b) a semi-transparent screen for displaying an image of image data provided to it with an adjustable degree of transparency to appear superimposed on structures seen through the screen;
   c) a tracking device for repeatedly measuring location and orientation of the semi-transparent screen relative to the dynamically changing subject position, and the dynamically changing observer viewpoint;
   d) a mechanical arm for adjustably holding the semi-transparent screen in a selected position between said observer viewpoint and said patient position such that a selected region is visible through the semi-transparent screen; and
   e) a workstation means coupled to the tracking device for receiving the location and orientation of the screen, operator viewpoint and patient position, and for creating an image from said imaging data, on the semi-transparent screen of internal structures consistent with the relative location and orientation of the semi-transparent screen the operator viewpoint, and the patient position.

2. The interactive medical apparatus of claim 1 further comprising:
   a) an invasive device having a position and orientation which is also measured by the tracking device; and
   b) a symbol generation means for superimposing a symbol on the semi-transparent screen indicating the position and orientation of the invasive device.

3. The interactive medical apparatus of claim 2 wherein the symbol generation means further comprises a means for displaying a ray indicating the current orientation of the invasive device and its proposed path into the internal structures of the patient.

4. The interactive medical apparatus of claim 1 wherein tracking device includes means to determine a first and second stereoscopic observer viewpoint and the workstation means creates an image relating to the first stereoscopic observer viewpoint, and further comprising:
   a) a second workstation means for creating a second image of said internal structures from the imaging data as viewed from the second stereoscopic observer viewpoint;
   b) stereoscopic display means having first and second apertures having adjustable opacity, synchronized with the semi-transparent screen for making the first aperture transparent and the second aperture opaque when the first computer generated image is being displayed, and for making the first aperture opaque and the second aperture transparent when the second computer generated image is being displayed, thereby simulating a 3D image of internal structures superimposed upon and external structures of said patient.

5. The interactive medical apparatus of claim 1 wherein the semi-transparent screen has a surface comprised of a material which may be written upon and erased.

6. A method of aiding an operator at a dynamically changing observer viewpoint to perform a medical procedure upon a patient at a dynamically changing subject position comprising the steps of:
   a) acquiring multi-dimensional medical imaging data from internal structures of said patient;
   b) positioning a free-standing semi-transparent screen at a selected location and orientation allowing a selected region of said patient to be viewed through the semi-transparent screen;
   c) measuring locations (x,y,z) and orientation angles $(\alpha, \phi, \theta)$ of the semi-transparent screen, said subject position, and said observer viewpoint;
   d) creating a computer generated image of the internal structures from the medical imaging data consistent with the measured locations (x,y,z) and orientation angles $(\alpha, \phi, \theta)$;
   e) displaying the computer generated image on the semi-transparent screen with a desired degree of transparency to create the illusion of internal structures superimposed upon said patient to assist the operator in said medical procedure.

7. The method of aiding an operator in a medical procedure of claim 6 wherein the step of acquiring multi-dimensional medical imaging data is performed in real-time by a medical imaging system.

8. The method of claim 6 wherein the step of creating a computer image comprises the step of:
   a) creating a pair of computer generated stereo images of the internal structures from the medical imaging data consistent with the measured locations and orientation angles; and
   b) the step of displaying the computer generated image comprises the step of: displaying the pair of computer generated images on the semi-transparent screen with a desired degree of transparency to create a stereographic illusion of internal structures superimposed upon said patient to assist the operator in said medical procedure.

9. The method of aiding an operator in a medical procedure of claim 8 further comprising the step of adjusting the distances and orientation angles of the pair of computer generated stereo images to correspond to the view of the patient by the operator.

* * * * *